US009468588B2

(12) United States Patent
Shemesh

(10) Patent No.: US 9,468,588 B2
(45) Date of Patent: Oct. 18, 2016

(54) VIAL ADAPTER ASSEMBLY IN DRUG MIXING SYSTEM

(75) Inventor: Eli Shemesh, Ashdod (IL)

(73) Assignee: Teva Medical Ltd., Ashdod (IL)

( * ) Notice: Subject to any disclaimer, the term of this patent is extended or adjusted under 35 U.S.C. 154(b) by 1715 days.

(21) Appl. No.: 12/706,044

(22) Filed: Feb. 16, 2010

(65) Prior Publication Data

US 2010/0217226 A1 Aug. 26, 2010

(51) Int. Cl.

| | |
|---|---|
| ***A61M 5/30*** | (2006.01) |
| ***A61J 1/20*** | (2006.01) |
| *A61M 37/00* | (2006.01) |
| *A61B 19/00* | (2006.01) |
| *A61M 5/32* | (2006.01) |
| *B67D 7/60* | (2010.01) |

(52) U.S. Cl.

CPC ............... *A61J 1/2096* (2013.01); *A61J 1/201* (2015.05); *A61J 1/2055* (2015.05); *A61J 1/2075* (2015.05); *A61J 1/2082* (2015.05)

(58) Field of Classification Search

CPC ........ A61M 5/30; A61M 37/00; A61M 5/32; B67D 7/60; B65D 5/72

USPC .................................. 604/405, 407, 411–416

See application file for complete search history.

(56) References Cited

U.S. PATENT DOCUMENTS

| | | | | |
|---|---|---|---|---|
| 4,735,608 A * | 4/1988 | Sardam | 604/89 |
| 5,049,129 A * | 9/1991 | Zdeb et al. | 604/85 |
| 7,354,427 B2 * | 4/2008 | Fangrow | 604/413 |
| 2007/0079894 A1 * | 4/2007 | Kraus et al. | 141/319 |
| 2008/0066739 A1 * | 3/2008 | LeMahieu et al. | 128/200.14 |

FOREIGN PATENT DOCUMENTS

| | | |
|---|---|---|
| DE | 7702734 | 9/1977 |
| WO | 2005/041846 | 5/2005 |
| WO | 2008/048631 | 4/2008 |

OTHER PUBLICATIONS

PCT Search Report PCT/US2010/024246.

Email communication with Chemviron Carbon Ltd. makers of Zorliex brand carbon cloth, dated Dec. 13, 2013.

* cited by examiner

*Primary Examiner* — Michele Kidwell
*Assistant Examiner* — Ilya Treyger
(74) *Attorney, Agent, or Firm* — Dekel Patent Ltd.; David Klein

(57) ABSTRACT

Apparatus for use in a drug mixing system including a vial adapter assembly including a main body element having a vial receiving portion and a needle puncturable port, the main body element including an axial hollow tubular portion which is in fluid flow engagement with a bore of a vial puncturing spike, the main body element further including a membrane support surface that supports a first membrane which is in fluid flow engagement with the vial puncturing spike via the bore and via a recess formed in an intermediate portion of the main body element, and a second membrane supported by a membrane support member and separated by a gap from the first membrane.

6 Claims, 3 Drawing Sheets

VIAL ADAPTER ASSEMBLY IN DRUG MIXING SYSTEM

FIELD OF THE INVENTION

The present invention relates to drug mixing systems generally, and particularly to a vial adapter assembly for use with a drug mixing system, which has a double membrane that allows free passage of air into the main body of the vial adapter, but prevents passage therethrough of liquid and air-borne particles, microorganisms and aerosol.

BACKGROUND OF THE INVENTION

Drug mixing systems are well known in the art. One particular drug mixing system is described in published PCT patent application WO 2005/041846, assigned to the current assignee of the present application, the disclosure of which is incorporated herein by reference. The drug system is commercially available from Teva Medical Ltd. and is sold under the brand name Tevadaptor. It is a system for safe compounding and administration of hazardous intravenous drugs. Tevadaptor minimizes the risk of exposure to hazardous drug substances, and eliminates the risk of needle stick injuries. The drug mixing system is intended for use with a luer fitted hypodermic syringe, and is particularly useful for handling toxic drugs such as antineoplastic drugs.

The Tevadaptor drug mixing system includes a receptacle port adapter that can be inserted into a port of a fluid receptacle, such as an IV bag. A vial adapter assembly is provided for connection to a vial containing a drug. A syringe adapter element may be attached to a syringe and to the receptacle port adapter and/or the vial adapter assembly. The receptacle port adapter, syringe adapter element and/or the vial adapter assembly may be vented to the atmosphere in a manner that prevents release to the atmosphere of possibly harmful contents of the vial in a liquid, solid or gaseous form.

The syringe adapter element may have a needle that fluidly communicates with the contents of the syringe. The needle does not normally protrude outwards, but rather is sealed inside the syringe adapter element by a septum. The syringe adapter element may be assembled onto the luer tip of the syringe. The needle of the syringe adapter element is now in fluid communication with the contents of the vial but the contents do not flow outwards because the needle is sealed inside by the septum.

Similarly, the vial adapter assembly may have a needle that fluidly communicates with the contents of the vial, wherein the needle does not normally protrude outwards, but rather is sealed inside the vial adapter assembly by a septum. The vial may be pushed onto the vial adapter assembly, wherein the needle of the vial adapter assembly punctures the septum of the vial. The vial adapter assembly may then be pushed onto the syringe adapter element, wherein the needle of the syringe adapter element punctures the septa of the syringe adapter element and the vial adapter assembly. This allows fluid to flow from the syringe through the needle of the syringe adapter element and through the needle of the vial adapter assembly to the vial.

After filling the vial with a desired amount of fluid, the vial adapter assembly may be separated from the syringe adapter element Immediately upon separation, the needle of the syringe adapter element and the needle of the vial adapter assembly are both sealed by their respective septa. In this manner, no fluid drips outwards.

SUMMARY OF THE INVENTION

The present invention seeks to provide an improved vial adapter assembly for the Tevadaptor drug mixing system, particularly a vial adapter assembly that has a double membrane that allows free passage of air into the main body of the vial adapter, but prevents passage therethrough of liquid and air-borne particles, microorganisms and aerosol.

There is thus provided in accordance with an embodiment of the present invention apparatus for use in a drug mixing system including a vial adapter assembly including a main body element having a vial receiving portion and a needle puncturable port, the main body element including an axial hollow tubular portion which is in fluid flow engagement with a bore of a vial puncturing spike, the main body element further including a membrane support surface that supports a first membrane which is in fluid flow engagement with the vial puncturing spike via the bore and via a recess formed in an intermediate portion of the main body element, and a second membrane supported by a membrane support member and separated by a gap from the first membrane. The first and second membranes may be hydrophobic and generally parallel to one another.

In accordance with an embodiment of the present invention the membrane support member is formed with vent holes. The membrane support member may include tabs that fit into grooves formed in the intermediate portion.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1A:
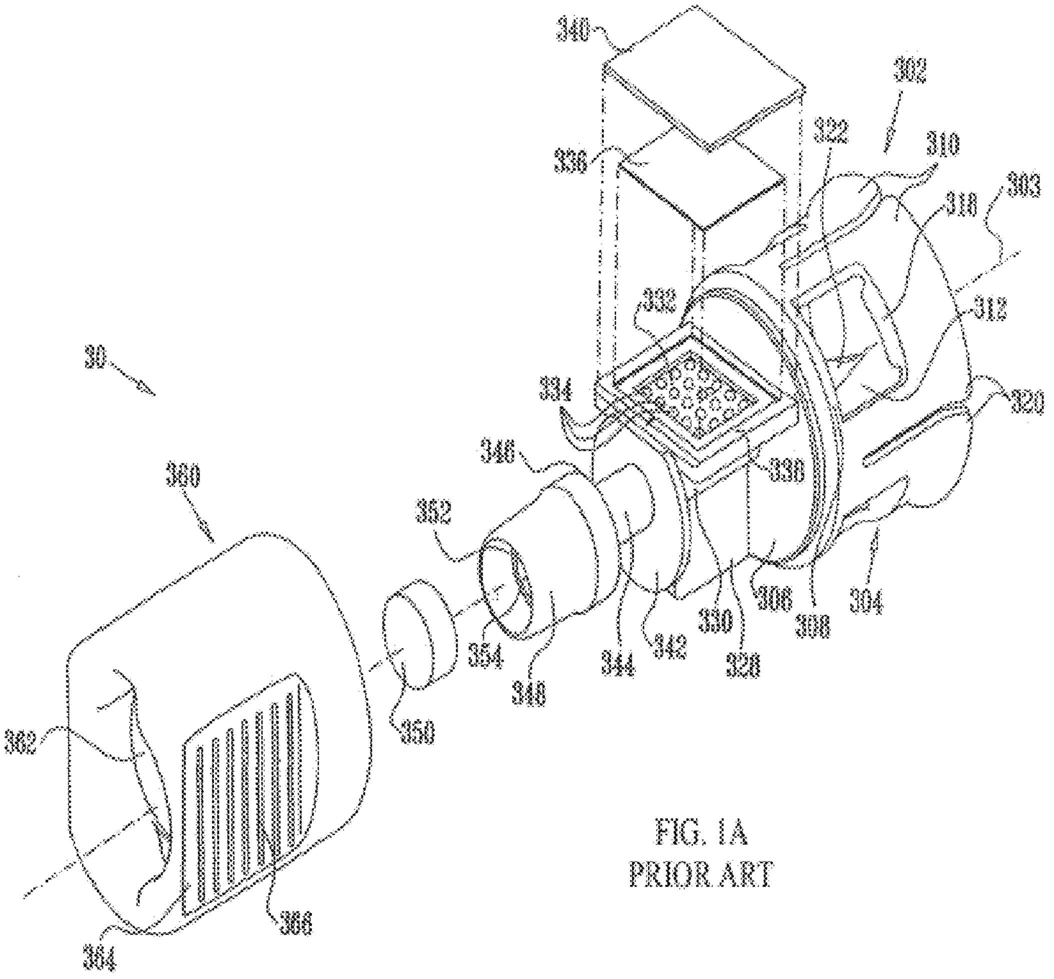
FIG. 1A PRIOR ART
FIGS. 1A and 1B are respective exploded and sectional illustrations of a vial adapter assembly of a drug mixing system of the prior art.
Figure 1B:
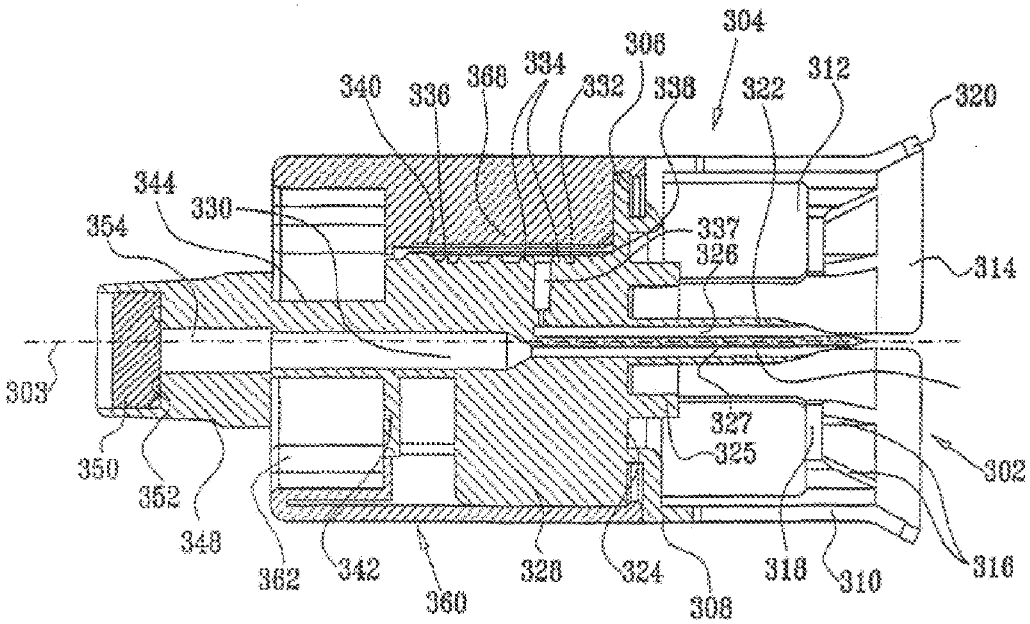
FIG. 1B PRIOR ART

Reference is now made to FIGS. 1A and 1B, which illustrate a vial adapter assembly 30 of a drug mixing system of the prior art, such as that described in published PCT patent application WO 2005/041846.

The vial adapter assembly 30 comprises a main body element 302 arranged generally about an axis 303. Main body element 302 may be integrally formed and injection molded of plastic.

Main body element 302 may include a rear portion 304, also referred to as a vial receiving portion, which is generally cylindrical and terminates in a forward wall 306. Rear portion 304 comprises a forward base section 308, rearward of which are preferably formed four tabs 310 each having a rectangular window 312.

Rearward of rectangular windows 312 and on an inner surface 314 of each of tabs 310 there are preferably formed two radially extending inwardly facing protrusions 316 each having an inclined surface. Protrusions 316 preferably terminate at a forward end thereof in an inwardly facing transversely extending protrusion 318. Rearward of protrusions 316, each of tabs 310 preferably includes an outwardly tapered portion 320.

A hollow vial puncturing spike 322 extends rearwardly from a rearward surface 324 of forward wall 306, and is surrounded by base section 308 and by tabs 310.

Rearward surface 324 additionally includes a circular cylindrical protrusion 325, surrounding puncturing spike 322. Two radially extending bores 326 and 327 extend through vial puncturing spike 322.

Forward of forward wall 306 of rear portion 304 there is formed an intermediate portion 328 which is generally rectangular, and includes axial hollow tubular portion 330 which is in fluid flow engagement with bore 327 of vial puncturing spike 322.

At a top surface of intermediate portion 328 and slightly recessed with respect thereto there is formed a membrane support surface 332, having formed thereon a plurality of generally evenly distributed spherical protrusions 334, which are adapted to support a first membrane 336 (preferably hydrophobic) and prevent it from excessive inflation and from cracking. Membrane 336 is adapted to allow free passage of air into the main body element 302, but to prevent passage therethrough of liquid and air-borne particles, microorganisms and aerosol. A preferred membrane 336 is Model VersaporR 0.2 microns, which is commercially available from Pall Corporation of New York, U.S.A.

Membrane 336 is in fluid flow engagement with vial puncturing spike 322 via bore 326 and via a recess 337 formed in intermediate portion 328.

A rim 338 surrounding support surface 332 is adapted to support an optional carbon cloth filter 340 and maintain it in a raised position above and spaced from membrane 336. Carbon cloth filter 340 is adapted to prevent toxic vapors from escaping from main body element 302, thus protecting users. A preferred carbon cloth filter 340 is Model No. Zorflex EMI, which is commercially available from Charcoal Cloth International Ltd. of Houghton-le-Spring, England.

Intermediate portion 328 terminates at a forward end thereof in a generally circular wall 342. Forward of circular wall 342 there is formed a hollow neck portion 344, which is in fluid flow engagement with hollow tubular portion 330 and with hollow vial puncturing spike 322. Hollow neck portion 344 terminates at a forward end thereof in a generally circular wall surface 346.

Forward of neck portion 344 there is formed a forward facing portion 348, also referred to as a needle puncturable port, which is adapted to sealingly accommodate a generally circular septum 350 on a seat 352 which is located at a forward end of portion 348. Forward facing portion 348 defines a central bore 354 which communicates between tubular portion 330 and septum 350.

Vial adapter assembly 30 preferably additionally includes a covering element 360 which supports and covers membrane 336 and carbon filter 340. Covering element 360 is a generally cylindrical, generally side-to-side symmetric, element and is preferably formed with a central opening 362 at a forward end thereof through which forward portion 348 extends.

Outer side surfaces 364 of covering element 360 are each formed with ribbed grip regions 366. An inner top surface 368 of covering element 360 is preferably flat, and is adapted to support the top surfaces of membrane 336 and carbon filter 340 and to prevent excessive inflation and cracking thereof.

Figure 2:
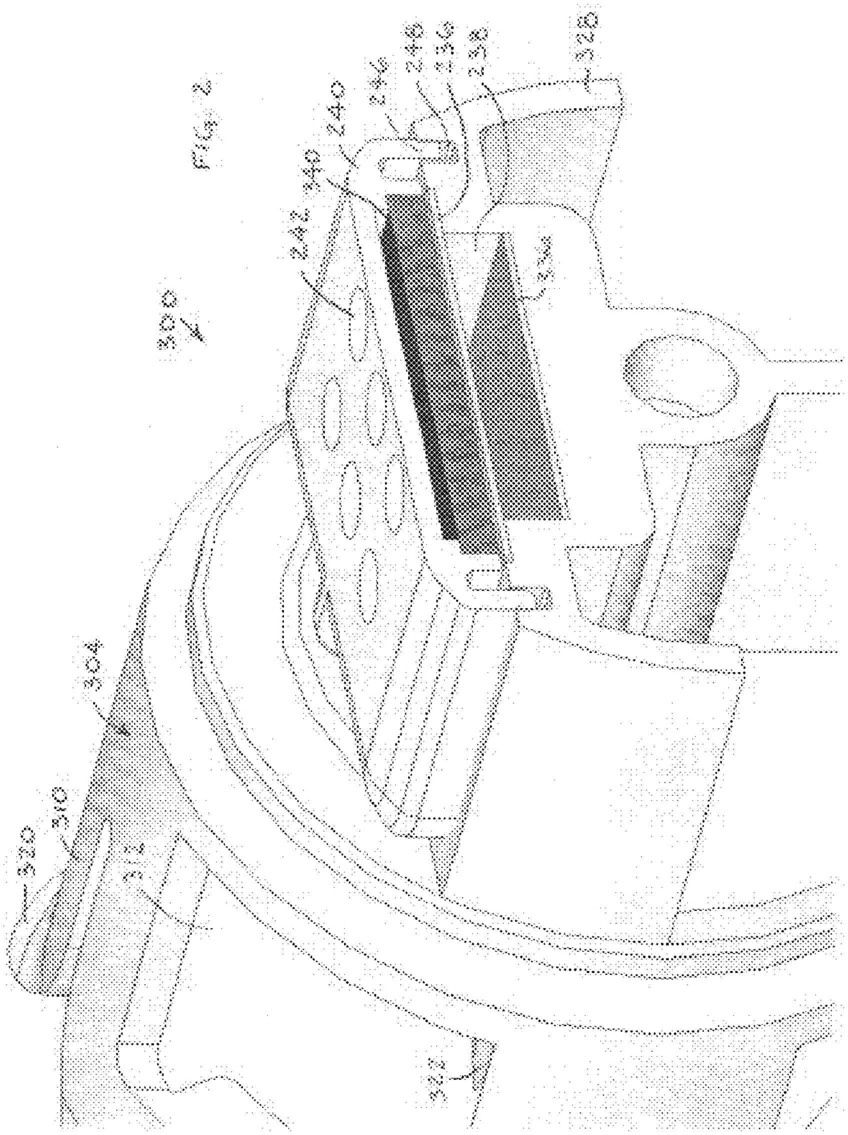
FIG. 2 is a simplified partially sectional illustration of a vial adapter assembly, constructed and operative in accordance with an embodiment of the present invention.

Reference is now made to FIG. 2, which illustrates a vial adapter assembly 300, constructed and operative in accordance with an embodiment of the present invention, with like elements to vial adapter assembly 30 being designated by like numerals.

Vial adapter assembly 300 differs from vial adapter assembly 30 in that vial adapter assembly 300 includes a second membrane 236 supported by a membrane support member 240. The second membrane 236 is separated by a gap 238 from first membrane 336. The first and second membranes 336 and 236 may be generally parallel to one another. Like the first membrane 336, the second membrane 236 may be hydrophobic.

The membrane support member 240 may include tabs 246 that snugly fit into grooves 248 formed in intermediate portion 328. Membrane support member 240 may be formed with vent holes 242.

The pair of membranes 236 and 336 allow free passage of air into the main body of the vial adapter, but prevent passage therethrough of liquid and air-borne particles, microorganisms and aerosol.

The carbon cloth filter 340 may be positioned above second membrane 236.

It is appreciated that various features of the invention which are, for clarity, described in the contexts of separate embodiments, may also be provided in combination in a single embodiment. Conversely, various features of the invention which are, for brevity, described in the context of a single embodiment, may also be provided separately or in any suitable subcombination.

What is claimed is:

1. Apparatus for use in a drug mixing system comprising:

a vial adapter assembly comprising a main body element having a vial receiving portion and a needle puncturable port;

said main body element comprising an axial hollow tubular portion which is in fluid flow engagement with a bore of a vial puncturing spike, said main body element further comprising a membrane support surface that supports a first membrane which is in fluid flow engagement with said vial puncturing spike via said bore and via a recess formed in an intermediate portion of said main body element; and a second membrane supported by a membrane support member and separated by a gap from said first membrane, and wherein said first and second membranes are hydrophobic.

2. The apparatus according to claim 1, wherein said first and second membranes are generally parallel to one another.

3. The apparatus according to claim 1, further comprising an adsorbent positioned above said second membrane.

4. The apparatus according to claim 1, wherein said membrane support member is formed with vent holes.

5. The apparatus according to claim 1, wherein said membrane support member comprises tabs that fit into grooves formed in said intermediate portion.

6. The apparatus according to claim 1, further comprising a carbon filter positioned above said second membrane.

* * * * *